US005230332A

United States Patent [19]

Strickland

[11] Patent Number: 5,230,332

[45] Date of Patent: Jul. 27, 1993

[54] METHODS AND APPARATUS FOR A MICRO-TRACHEAL CATHETER HUB ASSEMBLY

[75] Inventor: Richard D. Strickland, Sandy, Utah

[73] Assignee: Ballard Medical Products, Draper, Utah

[21] Appl. No.: 602,426

[22] Filed: Oct. 22, 1990

[51] Int. Cl.[5] .............................................. A61M 16/00

[52] U.S. Cl. .......................... 128/207.14; 128/207.15; 128/207.17; 606/1; 604/24; 604/283

[58] Field of Search ...................... 128/207.14, 207.15, 128/207.16, 207.17, DIG. 26; 604/83, 85, 86, 179, 283, 284, 905, 24

[56] References Cited

U.S. PATENT DOCUMENTS

| | | | |
|---|---|---|---|
| 2,127,215 | 8/1938 | Gwathmey | 128/208 |
| 2,624,341 | 1/1953 | Wallace | 128/350 |
| 2,786,469 | 3/1957 | Cohen | 128/351 |
| 2,912,982 | 11/1959 | Barsky | 128/351 |
| 2,991,787 | 7/1961 | Shelden et al. | 128/351 |
| 3,039,469 | 6/1962 | Fountain | 128/351 |
| 3,225,767 | 12/1965 | Smith | 128/351 |
| 3,319,622 | 5/1967 | Shiner | 128/2 |
| 3,599,642 | 8/1971 | Tindel | 128/351 |
| 3,788,305 | 1/1974 | Schreiber | 128/2 F |
| 3,884,242 | 5/1975 | Bazell et al. | 128/351 |
| 3,948,273 | 4/1976 | Sanders | 128/351 |
| 3,991,762 | 11/1976 | Radford | 128/276 |
| 4,022,219 | 5/1977 | Basta | 128/351 |
| 4,033,353 | 7/1977 | LaRosa | 128/207.15 |
| 4,036,210 | 7/1977 | Campbell et al. | 128/2 F |
| 4,037,605 | 7/1977 | Firth | 128/207.15 |
| 4,072,146 | 2/1978 | Howes | 128/2.05 D |
| 4,235,229 | 11/1980 | Ranford et al. | 128/207.15 |
| 4,239,042 | 12/1980 | Asai | 128/214.4 |
| 4,240,417 | 12/1980 | Holever | 128/203.12 |
| 4,315,505 | 2/1982 | Crandall et al. | 128/200.26 |
| 4,344,436 | 8/1982 | Kubota | 128/350 R |
| 4,351,328 | 9/1982 | Bodai | 128/202.16 |
| 4,416,273 | 11/1983 | Grimes | 128/207.16 |
| 4,434,963 | 3/1984 | Russell | 251/7 |
| 4,525,156 | 6/1985 | Benusa et al. | 604/28 |
| 4,557,261 | 12/1985 | Rügheimer | 128/202.27 |
| 4,569,344 | 2/1986 | Palmer | 128/207.16 |
| 4,574,798 | 3/1986 | Heitzman | 128/205.22 |
| 4,586,691 | 5/1986 | Kozlow | 251/7 |
| 4,595,005 | 6/1986 | Jinotti | 128/205.24 |
| 4,622,968 | 11/1986 | Persson | 128/305.3 |
| 4,627,433 | 12/1986 | Lieberman | 128/207.16 |
| 4,637,389 | 1/1987 | Heyden | 128/207 |
| 4,641,646 | 2/1987 | Schultz et al. | 604/283 |
| 4,649,913 | 3/1987 | Watson | 128/207.15 |
| 4,669,463 | 6/1987 | McConnell | 128/207.14 |
| 4,674,495 | 6/1987 | Orr | 128/207.14 |
| 4,674,496 | 6/1987 | Svadjian et al. | 128/207.16 |
| 4,681,100 | 7/1987 | Brychta et al. | 128/204.25 |
| 4,683,879 | 8/1987 | Williams | 128/207.16 |
| 4,716,901 | 1/1988 | Jackson et al. | 128/343 |
| 4,723,543 | 2/1988 | Beran | 128/207.14 |
| 4,739,756 | 4/1988 | Horn | 128/207.14 |
| 4,815,459 | 3/1989 | Beran | 128/207.14 |
| 4,827,921 | 5/1989 | Rugheimer | 128/202.27 |
| 4,838,255 | 6/1989 | Lambert | 128/202.16 |
| 4,846,191 | 7/1989 | Brockway et al. | 128/748 |
| 4,869,718 | 9/1989 | Brader | 604/164 |
| 4,886,496 | 12/1989 | Conoscenti et al. | 604/96 |

(List continued on next page.)

FOREIGN PATENT DOCUMENTS

| | | | |
|---|---|---|---|
| 8902761 | 4/1989 | World Int. Prop. O. | 128/207.14 |

*Primary Examiner*—Stephen C. Pellegrino
*Assistant Examiner*—Glenn Dawson
*Attorney, Agent, or Firm*—Workman, Nydegger & Jensen

[57] ABSTRACT

The present invention relates generally to apparatus and methods used in trans-tracheal oxygen therapy to permit a micro-tracheal catheter to be inserted into the throat, so that breathing efficiency may be enhanced through the introduction of oxygen directly into the patient's lungs. More particularly, this invention relates to an adapter for use on the outer end of the micro-tracheal catheter to connect the micro-tracheal catheter to an oxygen source through an oxygen supply hub while simultaneously and selectively permitting the introduction of a saline solution or other material into the patient's lungs through a second material supply hub.

13 Claims, 6 Drawing Sheets

U.S. PATENT DOCUMENTS

| | | | |
|---|---|---|---|
| 4,898,163 | 2/1990 | George | 128/200.26 |
| 4,953,547 | 9/1990 | Poole, Jr. | 604/283 |
| 4,981,466 | 1/1991 | Lumbert | 604/19 |
| 4,981,470 | 1/1991 | Bombeck, IV | 128/635 |
| 4,981,477 | 1/1991 | Schon et al. | 604/264 |
| 4,995,384 | 2/1991 | Keeling | 128/D. 26 |
| 5,031,613 | 7/1991 | Smith et al. | 128/207.14 |
| 5,054,482 | 10/1991 | Bales | 128/207.14 |
| 5,058,579 | 10/1991 | Terry et al. | 128/207.14 |
| 5,060,645 | 10/1991 | Russell | 128/207.14 |
| 5,060,646 | 10/1991 | Page | 128/207.14 |
| 5,062,420 | 11/1991 | Levine | 128/207.14 |
| 5,067,496 | 11/1991 | Eisele | 128/207.14 |

METHODS AND APPARATUS FOR A MICRO-TRACHEAL CATHETER HUB ASSEMBLY

BACKGROUND

1. Field of the Invention

The present invention relates generally to apparatus and methods for use in transtracheal oxygen therapy. More particularly, the present invention provides for a novel connector hub assembly which allows oxygen to be supplied through a micro-tracheal catheter while simultaneously introducing another material with the oxygen into the lungs of a patient.

2. The Background of the Invention

Patients suffering from chronic oxygen-dependent respiratory failure must have an almost constant supply of oxygen. Today, many patients with chronic oxygen-dependent respiratory failure use nasal cannulas as part of their oxygen therapy. With nasal cannula therapy, patients receive needed oxygen through tubes which extend from the oxygen supply into the nasal passages and are attached with a harness at the ears and nasal septum.

There are some disadvantages associated with nasal cannula therapy One disadvantage is that before the oxygen can reach the lungs, it must first pass through the nasal passages, the back of the mouth, and the vocal chords. When administered through this route, much oxygen escapes from the mouth and the nose and is wasted. Three problems result from this loss of oxygen. One is that the oxygen saturation level of the patient is lower than it would otherwise be if the oxygen had not been wasted. This makes it more difficult for the patient to exercise, and exercise is often an important component of recovery for such patients. A second problem is that since much of the oxygen is wasted, patients are forced to carry with them larger containers of oxygen than would otherwise be necessary. For many, this is not only burdensome, but immobilizing, particularly in the case of persons who may be seriously physically weakened due to age or illness. A third problem is the financial burden placed upon patients to purchase oxygen supplies that are depleted by inefficient delivery.

An additional problem with the use of typical nasal cannula devices is discomfort. A constant flow of dry, cold oxygen in the nasal passages causes drying of delicate nasal membranes. This drying can cause the nasal passage tissues to swell and become irritated. As a consequence, less oxygen is delivered through the swollen nasal passages making breathing more difficult so that frequently, a patient will attempt to breathe through the mouth, which further complicates the drying problem. This problem is especially acute during the night when oxygen saturation levels are already at their lowest.

In addition, because the nasal cannula is attached around the ears of the user, the harness often irritates the tops of the ears. Because of these side-effects of nasal cannula therapy, patients have been reluctant to continuously wear such nasal cannula devices as prescribed. Thus, the effectiveness of the therapy is reduced.

In addition to the inefficient use of oxygen with nasal cannula, the need to draw oxygen through the nasopharyngeal and laryngotracheal dead space contributes to dyspnea and leads to recruitment of the accessory muscles of respiration. The use of these muscles requires exertion which in turn increases the need for oxygen.

Devices and methods have been developed which solve many of these problems. One such method, called transtracheal oxygen delivery, uses a micro-tracheal catheter inserted into the trachea through the skin at the base of the throat. On the end of the catheter is attached a luer connector which couples the catheter through an oxygen supply tube to an oxygen source. With the use of this device, oxygen is neither lost nor wasted because it is delivered into the trachea directly above the lungs. Thus, oxygen delivery is more efficient. This efficiency allows patients to be more mobile because they may carry around smaller containers of oxygen. Another advantage is better oxygen saturation as a result of delivery closer to the lungs.

To overcome many of the disadvantages of other methods, micro-tracheal catheters were developed to have as little impact on a patient's lifestyle as possible. The catheter was developed to be as small as possible and still be capable of delivering the necessary one to six (1-6) liters per minute flow required by most adult patients. The supply tube from the oxygen supply may be concealed under the patient's clothing and the supply itself is often contained in an easy-to-carry and discrete container. Even the puncture and installation procedure itself takes little more than fifteen minutes and recovery is usually swift.

After local and topical anesthesia is administered, a puncture is made and the micro-tracheal catheter is inserted into the trachea between two of its upper cartilaginous rings. Insertion is usually accomplished with an internal needle or needle, guidewire, dilator technique.

The microtracheal catheter is slid over the guidewire into the bronchial tree. The guidewire reduces trauma and the risk of kinking.

At this point, the catheter is completely advanced into the trachea until the retention strap abuts the skin and the catheter is no longer visible. With the guidewire serving as a roentgenologic marker, chest radiographs can be performed to document the positioning of the catheter. The guidewire is then removed and the retention strap is sutured to the neck and secured around the patient's neck to retain the catheter in place. Oxygen is later attached and the previous method of oxygen delivery removed.

The benefits of the micro-tracheal catheter often include the restoration of smell and taste and occasionally libido. The appliance has little cosmetic intrusion and mobility is higher than with any other form of treatment. As a result of these benefits, patients often resume pretreatment activities and generally achieve a higher standard of life.

This device and method also solve the problem of irritation of the nose and face. Since the oxygen does not have to pass through the nose, the nasal tissues do not become dry and irritated. Further, there are no facial attachments to irritate or encumber the face and ears.

A further advantage of the micro-tracheal catheter and method is the fact that it assists the patient in breathing. Breathing requires a certain amount of work. If a patient has chronic obstructive lung disease, the amount of work needed to breathe is increased. This work is reduced by the delivery of oxygen directly to the lungs under the pressure of an oxygen tank. Thus, with transtracheal oxygen delivery a patient is able to work less to get the same volume of oxygen to the lungs.

The size of the micro-tracheal catheter requires a much smaller opening (0.2 to 0.3 cm long) than that required for transtracheal tubes formerly used and is, therefore, more cosmetically appealing than either nasal cannula or larger tracheal tubes.

As illustrated in FIG. 1, when a transtracheal catheter is placed in the trachea, it must be able to make an abrupt bend after the catheter passes through the neck of the patient so as to extend the distal end of the catheter down toward the lungs. This bend serves to assist in locating the microtracheal catheter at the back of the trachea and away from the more sensitive sides. Since transtracheal catheters are directly connected to the oxygen supply tube through the luer connector, or to the neck through sutures, no rotation of the oxygen supply tube in relation to the neck is allowed. If the catheter is not flexible enough and does not have sufficient circular memory and resiliency, certain kinds of abrupt action such as swallowing, turning the head, coughing and the like will tend to result in kinking, and possibly irritation to the sides of the trachea.

Another problem associated with transtracheal catheters arises from the direct introduction of oxygen into the trachea. Such introduction bypasses the natural moisturizing action of the upper respiratory tract. Oxygen dries the trachea and lungs and so, requires regular irrigation with saline solution. Irrigation loosens secretions, stimulates expectoration, and moisturizes the lungs.

With existing systems, irrigation is accomplished by disconnecting the patient from oxygen and instilling saline solution into the transtracheal catheter of the patient. Droplets of the saline solution then contact the carina, and that cough center is stimulated to violent coughing. While this coughing action helps to clear the bronchial pathways, loosens secretions and cleanses the respiratory tract, coughing involves the expenditure of work and therefore, is an oxygen consumptive activity. The period when a patient requires the most oxygen is exactly at the time that the oxygen is disconnected. This situation often results in hypoxia during instillation. Since instillation is required from two to four times daily, it is easy to see why patient compliance has historically been low.

Another problem associated with the droplet nature of the solution being introduced is its inability to penetrate into the lungs for any distance. The droplets remain consolidated and are carried back up in the violent coughing that accompanies their presence near the carina.

A new problem associated with the small size of the micro-tracheal catheter occurs during irrigation. As the oxygen pressure is disconnected and saline solution introduced, the mucous dislodged by the violent coughing often fouls the tip of the micro-tracheal catheter pluging the opening thereof. This plugging may require the extraction of the catheter for cleaning or an additional irrigation procedure. Extraction necessitates the discontinuation of oxygen delivery. Other means must be used, such as nasal cannula or masks, if the patient must endure without oxygen for period while the catheter is cleaned. In some early micro-tracheal catheters this operation was required several times a day. While more modern catheters are constructed of materials to resist mucous build-up and clogging, violent coughing continues to occasionally plug the micro-tracheal catheter tip when no oxygen flow is present.

Another problem arising from the small size of the micro-tracheal catheter is illustrated in FIG. 1. The relatively heavy oxygen supply line, because of its connection to the micro-tracheal catheter some distance from the throat, tends to move the catheter about the trachea. This movement causes irritation or tickling of the trachea and may eventually wear on the sensitive sides of the trachea as the catheter is jostled from its usual position resting on the rear of the trachea. This movement causes coughing and discomfort and may eventually create irritation to the sides of the trachea.

Many physicians take advantage of the ability of the micro-tracheal catheter to inject medication directly into the lungs. This process, will also require the discontinuation of oxygen to the patient with the same resultant lapse in oxygen delivery. The medication is injected into the micro-tracheal catheter with a syringe or other device and enters the lungs in droplet form. While this introduction method is preferred over oral introduction, penetration into the lungs is still limited by the droplet form of the medication.

BRIEF SUMMARY AND OBJECTS OF THE INVENTION

It is, therefore, an object of the present invention to provide apparatus and methods for the simultaneous introduction of oxygen and a material, such as a saline solution, into the lungs of a patient through a micro-tracheal catheter, avoiding in the process the hypoxic effects of disconnecting the oxygen supply of the patient.

It is another object of the present invention to provide apparatus and methods for the aerosolization of materials before introduction into the lungs to avoid the negative reaction of the carina to droplets and to increase penetration into the lungs.

It is a further object of the present invention to provide apparatus and methods capable of resisting blockage of the tip of a micro-tracheal catheter from mucous accumulating on the catheter or being coughed-up from the lungs.

A yet further object of the present invention is to provide apparatus and methods that resist forces applied to the oxygen supply tube from being transferred to the micro-tracheal catheter thereby causing irritation and discomfort.

It is yet another object of the present invention to provide apparatus and methods allowing a micro-tracheal catheter to rotate within the means used to retain it to the micro-tracheal opening.

A still further object of the present invention is to provide apparatus and methods allowing the simultaneous constant flow of oxygen and the instillation of a medication into the lungs of a patient.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

To achieve the foregoing objects, and in accordance with the invention as embodied and broadly described herein, the present invention is directed to an apparatus and methods of use involving a connector hub assembly for use on the outer end of a micro-tracheal catheter to connect the micro-tracheal catheter to a continuous supply of oxygen through an oxygen supply hub while simultaneously and selectively permitting the introduction of a saline or other medicamentary solution or material into the patient's lungs through a material supply hub.

To facilitate intermixing before introduction into the lungs, a mixing chamber is provided. This mixing chamber communicates with the micro-tracheal catheter and two hubs. A first oxygen supply hub provides means for attaching an oxygen supply tube for communication with a continuous supply of oxygen. A second material supply hub provides for selective introduction of materials to be intermixed with the continuous supply of oxygen in the mixing chamber and transported therewith to the lungs.

A housing encloses the mixing chamber, and is attached to both the oxygen supply and material supply hubs and the proximal end of the micro-tracheal catheter. In a presently preferred embodiment of the invention, the axis of the material supply hub is aligned with the axis of the mixing chamber to provide direct access to the mixing chamber and micro-tracheal catheter. The oxygen supply hub axis is oriented at an angle to the mixing chamber and material supply hub to form a Y connection. Upon connection to an oxygen supply tube and oxygen supply, the oxygen supply hub provides a constant flow of oxygen to the patient. If the introduction of a material, such as a saline solution or other medication or material is desired, the material supply hub is opened by removing therefrom a tethered cap, and a device, such as a syringe, is used to introduce the material into the constant stream of oxygen flowing through the mixing chamber.

The constant flow of oxygen through the mixing chamber and the micro-tracheal catheter ensure that the tip of the catheter remain clear as mucous is coughed up from the lungs.

The presently preferred embodiment of the present invention provides for rotation of the connector hub assembly within a restraining device used for maintaining contact between the connector hub assembly and the micro-tracheal opening in the trachea of the patient. This rotational ability allows the connector hub assembly to be used with the oxygen supply on either side of the patient and redirects forces applied by movement of the neck into the more rigid oxygen supply tube instead of being transferred into the micro-tracheal catheter. This arrangement not only allows the patient to choose the oxygen supply placement, but also lessens the possibility of chaffing inside the trachea from movements of the neck.

The connector hub assembly is located in direct contact with the throat of the patient. This placement allows the neck to absorb pivoting forces applied to the connector hub assembly by any motion of the oxygen supply tube, which in turn lessens movement of the micro-tracheal catheter inside of the trachea. Reduced chaffing of the interior of the trachea results.

In keeping with the desire to limit the movement of the micro-tracheal catheter inside the trachea of the patient, the presently preferred embodiment also provides straps for limiting the movement of the oxygen supply tube.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered limiting of its scope, the invention and the presently understood best mode for making and using the invention will be described and explained with additional specificity and detail through the use of the accompanying drawings in which.

DETAILED DESCRIPTION OF THE PREFERRED EMBODIMENTS

Figure 1:
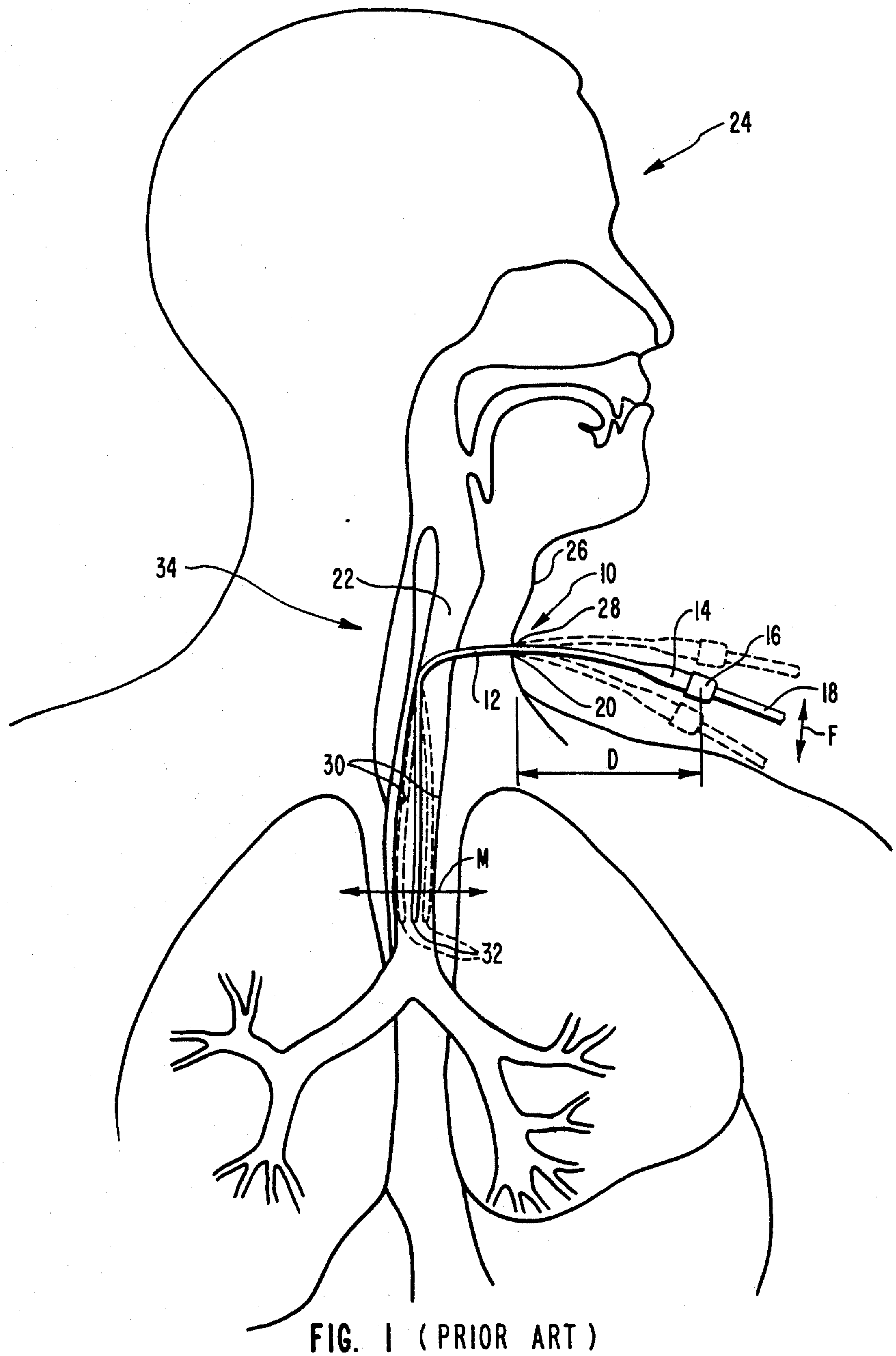
FIG. 1 is a schematic view showing a patient with a prior art device inserted through a micro-tracheal opening.

FIG. 1 illustrates a prior art device 10 comprised of a micro-tracheal catheter 12 joined at a proximal end 14 to an oxygen supply joint 16 and an oxygen supply tube 18. Prior art device 10 is inserted through a puncture wound 20 into a trachea 22 of a patient 24. FIG. 1 illustrates in dashed lines the movement caused to micro-tracheal catheter 12 by the prior art. In prior art device 10, oxygen supply tube 18 is connected to micro-tracheal catheter 12 at a distance D from a throat 26. Distance D allows oxygen supply tube 18 to act as a lever arm translating forces F along micro-tracheal catheter 12 to a puncture site 28. Puncture site 28 acts as a pivot point to translate movement caused by forces F to be translated into pivoting forces applied to micro-tracheal catheter 12. FIG. 1 illustrates in dashed lines the pivoting action of micro-tracheal catheter 12. The movement of micro-tracheal catheter 12 causes chaffing against a trachea side 30 causing irritation. The movement of a distal end 32 of micro-tracheal catheter 12 is directly proportional to the movement of oxygen supply tube 18. Movements in oxygen supply tube 18 are transferred to puncture site 28 where torsion may be developed as a result of the direct connection between oxygen supply tube 18 and micro-tracheal catheter 12. No allowance is made to relieve puncture site 28 of the torsional forces applied on it. Movements caused by motion in a neck 34 are also directly transferred into micro-tracheal catheter 12 at puncture site 28.

Figure 2:
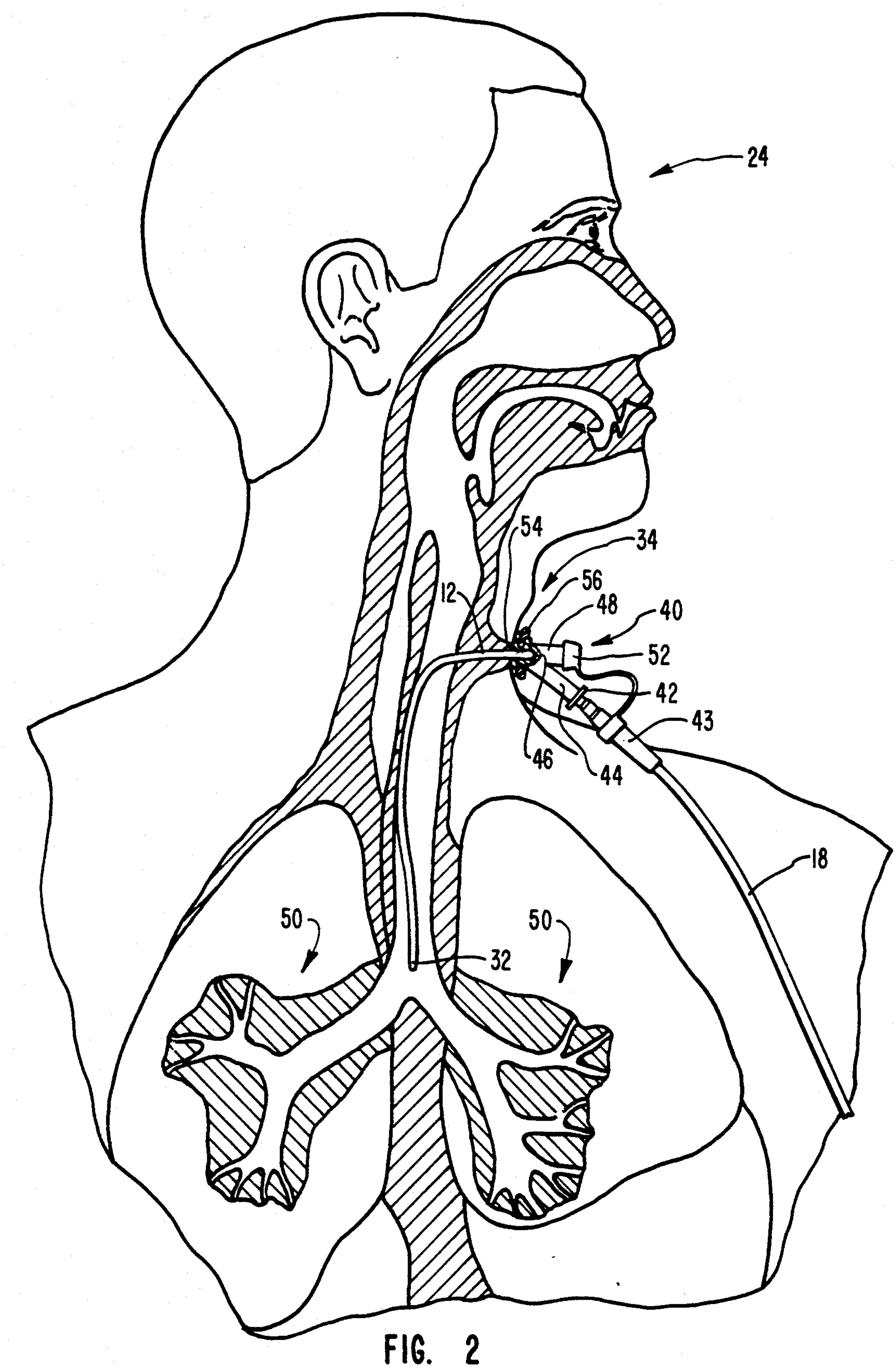
FIG. 2 is a schematic view of one presently preferred embodiment of the present invention attached to a micro-tracheal catheter placed in the trachea of a patient.

In FIG. 2, a connector hub assembly 40, incorporating teachings of the present invention is coupled to oxygen supply tube 18 with a male luer slip fitting 42 and a supply adaptor 43 at an oxygen supply hub 44. Oxygen supply tube 18 has been reduced at this point to allow easier concealment under clothing and to lessen the weight and forces transferred to connector hub assembly 40. Oxygen passes from oxygen supply tube 18, through supply adaptor 43 and male luer slip fitting 42 and through an opening in oxygen supply hub 44. After flowing through oxygen supply hub 44, oxygen enters a mixing chamber 46 which communicates freely with microtracheal catheter 12, a material supply hub 48, and oxygen supply hub 44. Oxygen then passes through micro-tracheal catheter 12 and exits distal end 32 into trachea 22 of patient 24. A tethered cap 52 closes the opening in material supply hub 48 when material supply hub 48 is not in use. FIG. 2 illustrates the proximity of connector hub assembly 40 to neck 34 of patient 24. Distance D as seen in FIG. 1 is not present in FIG. 2. Connector hub assembly 40 abuts throat 26 to reduce the lever arm of oxygen supply tube 18. An attaching button 54 with a hole therein for passage of micro-tracheal catheter 12 retains a strap 56 to connector hub assembly 40.

Figure 4:
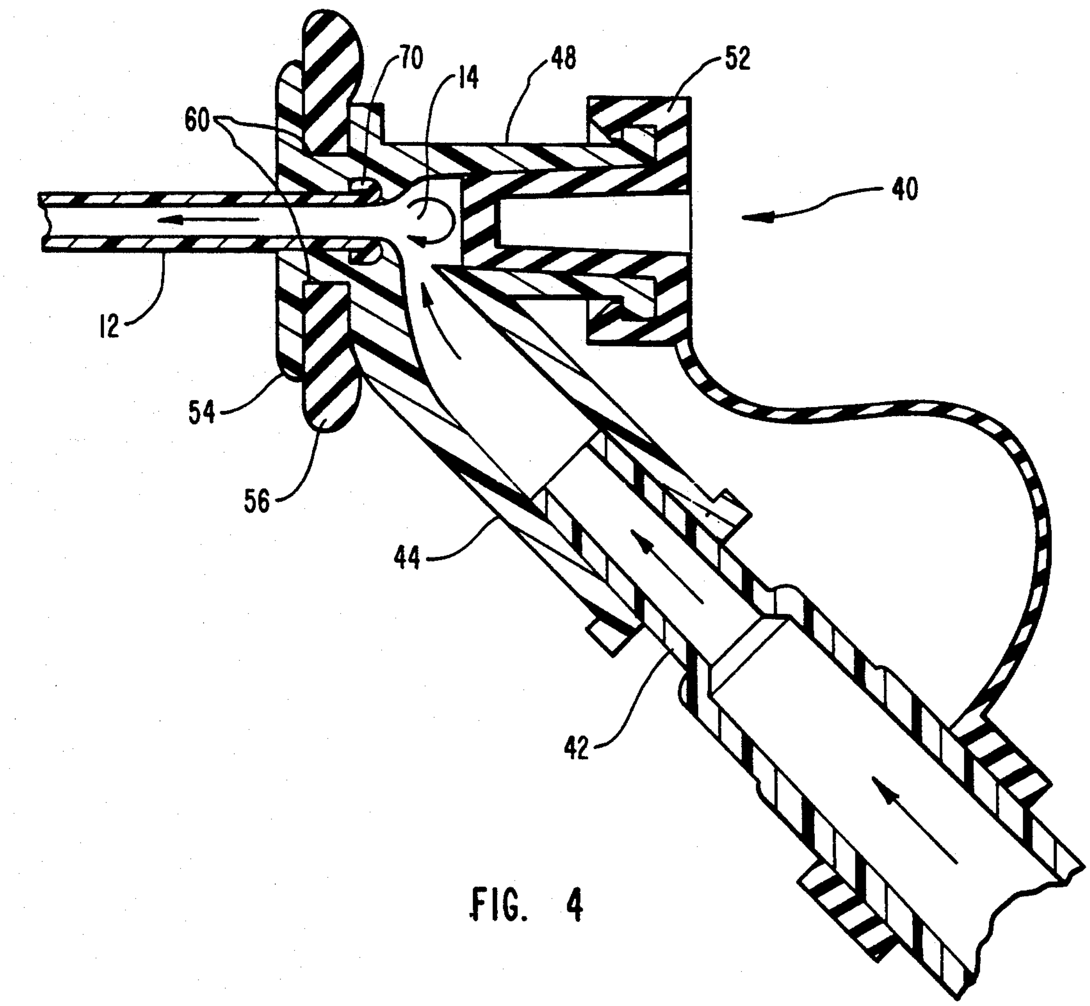
FIG. 4 is a cross-sectional view taken along line 4—4 of FIG. 3, illustrating the connection of the oxygen supply tube inside of the oxygen supply hub and the interrelationship of the micro-tracheal catheter, mixing chamber, oxygen supply hub and the material supply hub.

Turning now to FIG. 4, a hole 60 in strap 56 allows connector hub assembly 40 to rotate about the longitudinal axis of micro-tracheal catheter 12 while being retained to strap 56 by attaching button 54.

Figure 3:
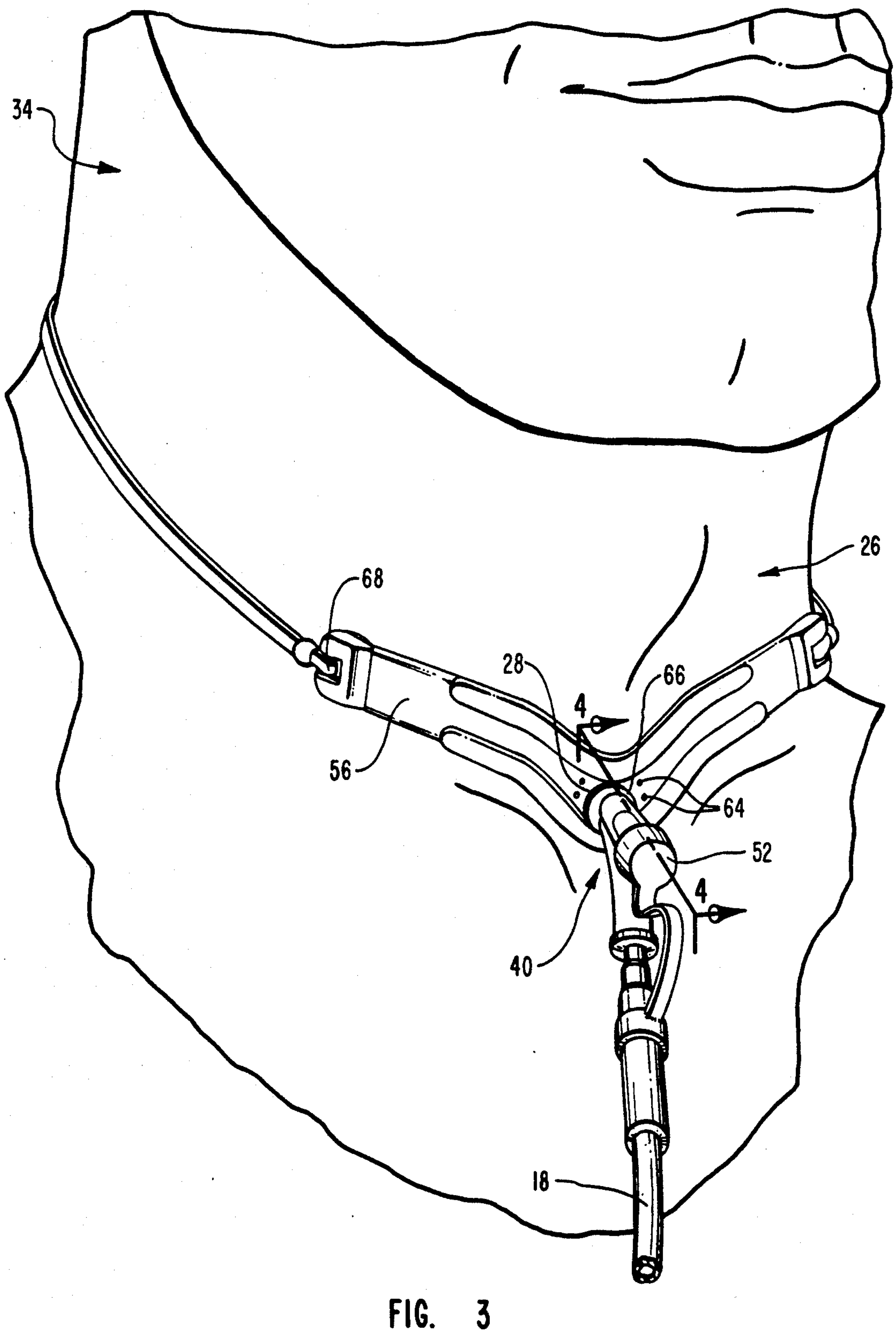
FIG. 3 is an enlarged prospective view of a preferred embodiment of the present invention illustrating the placement of the present invention at the throat of a patient.

As shown in FIG. 3, the placement of connector hub assembly 40 is further illustrated. Strap 56 stabilizes connector hub assembly 40 against throat 26. Suture holes 64 hold strap 56 to neck 34. Torsional movements applied to oxygen supply tube 18 are transferred to connector hub assembly 40. These torsional forces are then allowed to dissipate at rotational area 66. Rotational area 66 is the junction of connector hub assembly 40 and strap 56. Connector hub assembly 40 is allowed to rotate within strap 56 at rotational area 66 instead of transferring those torsional forces into neck 34 and puncture site 28. As seen in FIG. 3, retention means for retaining connector hub assembly 40 to throat 26 of patient 24 may comprise more than one element. In the illustrated embodiment of the present invention, strap 56 is provided with attachment holes 68 for connection to a further strap or chain. This arrangement retains connector hub assembly 40 snugly against throat 26 to allow neck 34 to absorb pivotal forces transferred from connector hub assembly 40 because of its contact with and close proximity to throat 26.

As illustrated in FIG. 4, connector hub assembly 40 has within it passageways communicating between oxygen supply hub 44, material supply hub 48, mixing chamber 46 and micro-tracheal catheter 12. Tethered cap 52 closes the opening in material supply hub 48 when not in use. Micro-tracheal catheter 12 is mechanically locked in place in connector hub assembly 40 by flaring proximal end 14 into a tab 70. As shown with arrows in FIG. 4, the coupling of male luer slip fitting 42 and oxygen supply hub 44 allows oxygen to flow through oxygen supply hub 44 into mixing chamber 46 and out through micro-tracheal catheter 12 into trachea 22 of patient 24. In the illustrated embodiment, tethered cap 52 is tethered to supply adaptor 43 although it will be appreciated that other locations could also assure the retention of tethered cap 52; for example, cap 52 could also be tethered to the material supply hub. Hole 60 in strap 56 allows torsional forces applied to connector hub assembly 40 by oxygen supply tube 18 to be translated into rotational movement of the connector hub assembly instead of being transferred to strap 56 and puncture site 28 to which strap 56 is sutured. The longitudinal axis of material supply hub 48 is aligned with the longitudinal axis of micro-tracheal catheter 12 forming a line through mixing chamber 46. The longitudinal axis of oxygen supply hub 44 is aligned at an angle to the longitudinal axis of material supply hub 48 forming a Y within connector hub assembly 40.

Figure 5:
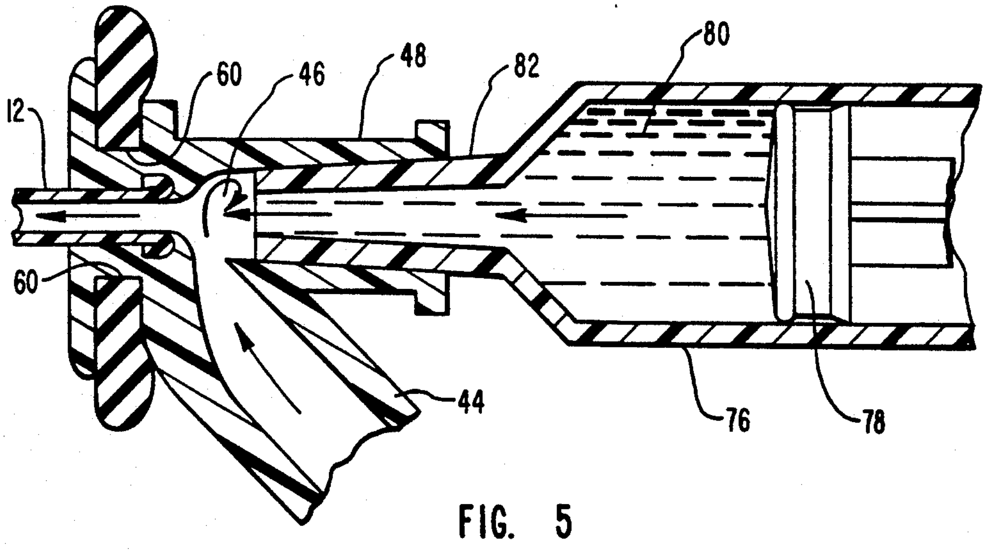
FIG. 5 is a cross-sectional view taken along line 4—4 of FIG. 3, illustrating the material supply hub and related structures.

FIG. 5 illustrates the introduction of material through material supply hub 48 by a syringe 76. The materials can be a powder, a gas, or can be from a metered dose inhalant. As can be seen in FIG. 4, a tethered cap 52 covers the opening in material supply hub 48 when it is not in use. In FIG. 5, tethered cap 52 has been removed in preparation for use of material supply hub 48. A material 80 introduced by syringe 76 is intermixed and becomes aerosolized in mixing chamber 46 with a continuous flow of oxygen from oxygen supply hub 44. This continuous flow of oxygen is illustrated with arrows as is the flow of material from syringe 76. A plunger 78 compresses material 80 and forces material 80 out of an injector 82 and into mixing chamber 46 to be intermixed with and aerosolized by the continuous stream of oxygen from oxygen supply hub 44. Material 80 after intermixing, is forced out of mixing chamber 46 and into proximal end 14 of micro-tracheal catheter 12, through micro-tracheal catheter 12 and into trachea 22. The Y orientation of material supply hub 48, oxygen supply hub 44 and micro-tracheal catheter 12 can be seen within connector hub assembly 40.

Figure 6:
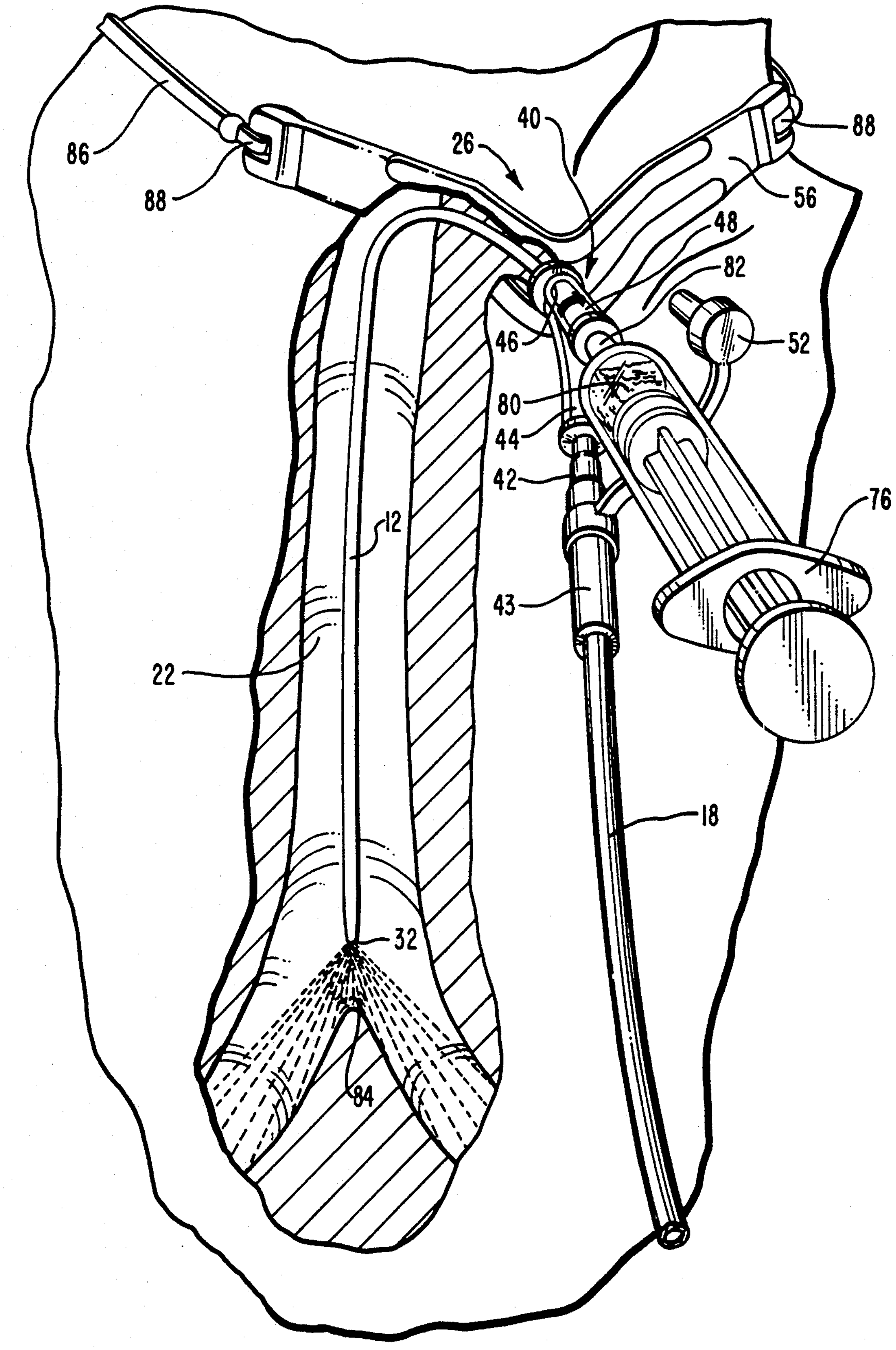
FIG. 6 is sectional view illustrating the introduction of a material through the material supply hub of a presently preferred embodiment of the present invention.

FIG. 6 illustrates the introduction of material 80 through material supply hub 48. Plunger 78 forces material 80 out of syringe 76 through injector 82 into material supply hub 48. Material 80 is intermixed with a constant stream of oxygen flowing from oxygen supply tube 18, through oxygen supply hub 44 and into mixing chamber 46. Upon intermixing, material 80 will be forced by the continuous passage of oxygen through mixing chamber 46 and into micro-tracheal catheter 12. Material 80 will then flow through micro-tracheal catheter 12 until material 80 exits through distal end 32. Material 80 and the oxygen that is intermixed with material 80 will enter trachea 22 in an aerosolized form and be drawn deep into the lungs of patient 24. The aerosolized form of material 80 allows it to remain suspended in the breath of patient 24 longer than droplets. In addition, aerosolized material 80 will not irritate a carina 84 thereby avoiding the violent coughing associated with irritation of the carina cough center. Tethered cap 52 is shown attached to supply adaptor 43 and removed from material supply hub 48. Strap 56 holds connector hub assembly 40 snugly against throat 26 to allow throat 26 to absorb much of the pivotal force applied by connector hub assembly 40. The broad resilient strap 56 is joined to a smaller portion of the retention means by smaller strap 86. It will be appreciated that other retention means may be employed to retain connector hub assembly 40 to neck 34. Smaller strap 86 is attached to strap 56 at attachment points 88. It will be appreciated that other devices may be used to inject material 80 into material supply hub 48.

Figure 7:
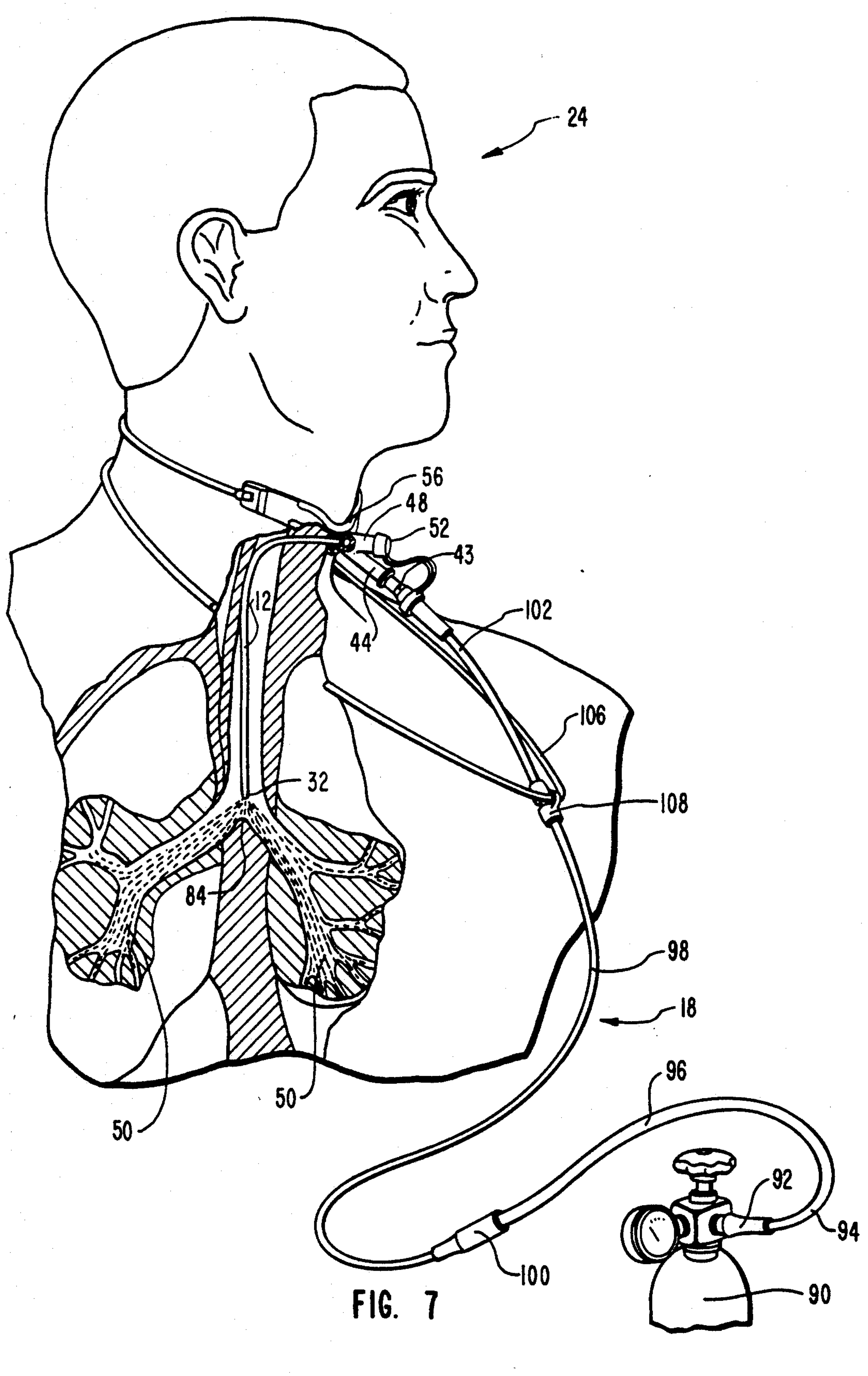
FIG. 7 is a perspective view with portions broken away particularly illustrating placement of the transtracheal catheter in a patient's trachea, and which illustrates the elements of a system for simultaneously introducing oxygen and a material through a micro-tracheal catheter.

FIG. 7 illustrates a system for simultaneously introducing oxygen and material 80 through micro-tracheal catheter 12. An oxygen supply 90 is connected to oxygen supply tube 18 by an oxygen supply connector 92 at a source end 94. Oxygen supply tube 18 is divided into a portion with a larger bore 96 for durability and a portion with a smaller bore 98 for ease of concealment under clothing. Oxygen flowing from oxygen supply 90 flows first through larger bore 96 to a reducing female oxygen bib 100 where the bore is reduced to that of smaller bore 98. The oxygen flow leaves smaller bore 98 at a delivery end 102 where it enters oxygen supply hub 44 through a male luer slip fitting 43 and passes through micro-tracheal catheter 12 and into the lungs 50 of patient 24. A restraint strap 106 attaches at one end to the body of patient 24 and at the other end to a friction cuff 108 slidably attached to oxygen supply tube 18 to reduce the communication of stresses placed on the oxygen supply tube from being transferred to connector hub assembly 40. Retention strap 56 maintains contact between connector hub assembly 40 and throat 26 of patient 24. Tethered cap 52 is tethered to oxygen supply tube 18 and covers material supply hub 48 when not in use.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Patent is:

1. A connector hub assembly connected to an ambulatory user's throat, said connector hub assembly adapted for coupling a micro-tracheal catheter to a supply of oxygen and to a supply of material to be mixed with oxygen so as to be supplied through the catheter without interrupting the supply of oxygen, said connector hub assembly comprising:

an oxygen supply hub having two ends, one end adapted to be coupled to the supply of oxygen; and a material supply hub having two ends, one end adapted to be coupled to the supply of material, and the other end joined to said oxygen supply hub at a junction so as to define a mixing chamber means for aerosolizing and intermixing the material with the oxygen prior to forcing the intermixed material and oxygen into the catheter, said mixing chamber means communicating with the other end of said oxygen supply hub, and the mixing chamber means at the end of the material supply hub being configured to be held adjacent to the user's throat, and with said end defining the mixing chamber means adapted to be attached to the catheter at the point where the catheter emerges from the user's throat, the material when introduced into the material supply hub becoming mixed in the mixing chamber means with the oxygen and transported therewith through the micro-tracheal catheter and into the lungs of the user.

2. A connector hub assembly as defined in claim 1, wherein said material supply hub has a cap fitted to close said one end of the material supply hub when not in use.

3. A connector hub assembly as defined in claim 1, wherein a cap is tethered to the hub assembly.

4. A connector hub assembly as defined in claim 1, wherein said hubs together form a unitary housing.

5. A connector hub assembly as defined in claim 4, wherein said housing comprises a Y shaped structure.

6. A connector hub assembly as defined in claim 5, wherein:

(a) said material supply hub comprises a material supply leg of said Y shaped structure;

(b) said oxygen supply hub comprises an oxygen supply leg of said Y shaped structure; and (c) one of said legs is releasably couplable to one of said supplies.

7. A connector hub assembly connected to an ambulatory user's throat, said connector hub assembly adapted for coupling a micro-tracheal catheter to a supply of oxygen and to a supply of material to be mixed with oxygen so as to be supplied through the catheter without interrupting the supply of oxygen, said connector hub assembly comprising:

an oxygen supply hub having two ends, one end adapted to be coupled to the supply of oxygen;

a material supply hub having two ends, one end adapted to be coupled to the supply of material, and the other end joined to said oxygen supply hub at a junction so as to define a mixing chamber means for aerosolizing and intermixing the material with the oxygen prior to forcing the intermixed material and oxygen into the catheter, said mixing chamber means communicating with the other end of said oxygen supply hub, and the mixing chamber means at the end of the material supply hub being configured to be held adjacent to the user's throat, and with said end defining the mixing chamber means adapted to be attached to the catheter at the point where the catheter emerges from the user's throat, the material when introduced into the material supply hub becoming mixed in the mixing chamber means with the oxygen and transported therewith through the micro-tracheal catheter and into the lungs of the user; and retention means for retaining the connector hub assembly against the throat of the user while allowing the connector hub assembly to be rotated relative to said retention means at a point of attachment adjacent the user's throat.

8. A connector hub assembly as defined in claim 7, wherein said retention means comprises a strap of flexible material joined to the connector hub assembly.

9. A connector hub assembly as defined in claim 8, wherein said strap further comprises suture holes formed near the joint with the connector hub assembly.

10. A connector hub assembly as defined in claim 9, wherein said strap further comprises means for securing the strap to the throat of the user.

11. A connector hub assembly as described in claim 9, wherein said strap further comprises rotation means for allowing torsional forces to move the connector hub assembly while retained to the throat.

12. A connector hub assembly as described in claim 11, wherein said rotation means comprises:

(a) an attaching button affixed to the connector hub assembly; and (b) a hole formed in the strap allowing rotational movement of the connector hub assembly about the attaching button.

13. A connector hub assembly connected to an ambulatory user's throat, said connector hub assembly adapted for coupling a micro-tracheal catheter to a supply of oxygen and to a supply of material to be mixed with oxygen so as to be supplied through the catheter without interrupting the supply of oxygen, said connector hub assembly comprising:

an oxygen supply hub having two ends, one end adapted to be coupled to the supply of oxygen;

a material supply hub having two ends, one end adapted to be coupled to the supply of material, and the other end joined to said oxygen supply hub at a junction so as to define a mixing chamber means for aerosolizing and intermixing the material with the oxygen prior to forcing the intermixed material and oxygen in to the catheter, said mixing chamber means communicating with the other end of said oxygen supply hub, and the mixing chamber means at the end of the material supply hub being configured to be held adjacent to the user's throat, and with said end defining the mixing chamber adapted to be attached to the catheter at the point where the catheter emerges from the user's throat, the material when introduced into the material supply hub becoming mixed i the mixing chamber means with the oxygen and transported therewith through the micro-tracheal catheter and into the lungs of the user;

a retention strap comprised of a pliable, resilient material in which holes are formed for attachment to a chain;

an attaching button means affixed to the retention strap for allowing rotational movement of the connector hub assembly; and a cap fitted to close said one end of the material supply hub when not in use.

* * * * *

UNITED STATES PATENT AND TRADEMARK OFFICE

CERTIFICATE OF CORRECTION

PATENT NO. : 5,230,332

DATED : July 27, 1993

INVENTOR(S) : RICHARD D. STRICKLAND

It is certified that error appears in the above-indentified patent and that said Letters Patent is hereby corrected as shown below:

Column 3, line 56, "pluging" should be --plugging--
Column 3, line 61, "period" should be --periods--
Column 12, line 3, "i" should be --in--

Signed and Sealed this

Fifteenth Day of March, 1994

Attest:

Bruce Lehman

BRUCE LEHMAN

*Attesting Officer*

*Commissioner of Patents and Trademarks*